(12) United States Patent
Singhal et al.

(10) Patent No.: US 7,124,637 B2
(45) Date of Patent: Oct. 24, 2006

(54) DETERMINING AMPLITUDE LIMITS FOR VIBRATION SPECTRA

(75) Inventors: Ashish Singhal, Glendale, WI (US);
John E. Seem, Glendale, WI (US);
Mark J. Muench, Milwaukee, WI (US)

(73) Assignee: Johnson Controls Technology Company, Holland, MI (US)

( * ) Notice: Subject to any disclaimer, the term of this patent is extended or adjusted under 35 U.S.C. 154(b) by 0 days.

(21) Appl. No.: 10/805,807

(22) Filed: Mar. 22, 2004

(65) Prior Publication Data

US 2005/0204818 A1 Sep. 22, 2005

(51) Int. Cl.
*G01N 29/46* (2006.01)

(52) U.S. Cl. .............................. 73/659; 73/579; 73/599; 73/602

(58) Field of Classification Search ................ 73/579, 73/597, 598, 599, 600, 602, 659, 660; 702/56, 702/183, 179, 180, 33–36, 58, 59, 182–185
See application file for complete search history.

(56) References Cited

U.S. PATENT DOCUMENTS

| | | | | |
|---|---|---|---|---|
| 4,931,949 | A * | 6/1990 | Hernandez et al. | 702/35 |
| 5,086,775 | A * | 2/1992 | Parker et al. | 600/453 |
| 5,922,963 | A * | 7/1999 | Piety et al. | 73/659 |
| 6,138,045 | A * | 10/2000 | Kupinski et al. | 600/425 |
| 6,208,944 | B1 * | 3/2001 | Franke et al. | 702/56 |
| 6,301,572 | B1 * | 10/2001 | Harrison | 706/52 |
| 6,314,204 | B1 * | 11/2001 | Cham et al. | 382/228 |
| 6,370,957 | B1 * | 4/2002 | Filippenko et al. | 73/660 |
| 6,438,981 | B1 * | 8/2002 | Whiteside | 62/228.1 |
| 6,629,058 | B1 * | 9/2003 | Komura et al. | 702/183 |
| 6,651,012 | B1 * | 11/2003 | Bechhoefer | 702/34 |
| 6,662,584 | B1 * | 12/2003 | Whiteside | 62/230 |
| 6,697,759 | B1 * | 2/2004 | Saarinen et al. | 702/145 |
| 6,792,360 | B1 * | 9/2004 | Smulders et al. | 702/35 |
| 6,816,810 | B1 * | 11/2004 | Henry et al. | 702/179 |
| 6,980,910 | B1 * | 12/2005 | Shen et al. | 702/56 |
| 2005/0021212 | A1 * | 1/2005 | Gayme et al. | 701/99 |

OTHER PUBLICATIONS

Diebold, F. X.; "Elements of Forecasting"; South-Western College Publishing, Cincinnati, OH (1998); pp. 30-31.
Iglewicz, B. and Hoaglin, D. C.; "How to Detect and Handle Outliers"; American Society for Quality; Milwaukee, WI (1993); pp. 32-33.
Kunt, M.; "Digital Signal Processing"; Artech House; Norwood, MA (1986); pp. 125-143.
Montgomery, D. C. and Runger, G. C.; "Applied Statistics and Probability for Engineers"; John Wiley; NY (1994); Chapter 14; pp. 831-865.
Sheskin, D. J.; Handbook of Parametric and Nonparametric Statistical Procedures; Chapman & Hall/CRC; Boca Raton, FL; $2^{nd}$ edn. (2000); pp. 390-392.

(Continued)

*Primary Examiner*—Hezron Williams
*Assistant Examiner*—Jacques Saint-Surin
(74) *Attorney, Agent, or Firm*—Foley & Lardner LLP

(57) ABSTRACT

A method for determining vibration amplitude limits of a mechanical device. The method comprises identifying a mechanical device and a frequency range for a spectrum to be analyzed, retrieving vibration spectra comprising individual spectrum for the mechanical device and the frequency range, calculating frequency for the individual spectrum, and identifying the individual spectrum with the smallest number of frequency lines. In addition, the method comprises calculating noise bandwidths and a largest noise bandwidth, removing outlier data, calculating conditional kernel density, and calculating vibration amplitude limits to detect faults in the mechanical device.

21 Claims, 12 Drawing Sheets

OTHER PUBLICATIONS

Technical Associates; "Concentrated Vibration Signature Analysis and Related Condition Monitoring Techniques"; Technical Associates of Charlotte, P.C.; Charlotte, NC (2002); Chapter 3.

Zani, S., Riani, M. and Corbellini, A.; "Robust Bivariate Boxplots and Multiple Outlier Detection"; Computational Statistics & Data Analysis; 28 (1998); pp. 257-270.

Rosner, B.; "Percentage Points for a Generalized ESD Many-Outlier Procedure"; Technometrics; 25 (1983); pp. 162-172.

Sheather, S. J. and Jones, M. C.; "A Reliable Data-Based Bandwidth Selection Method for Kernel Density Estimation"; J. Royal Statistical Soc. Ser.; B; 53 (1991) pp. 683-690.

Watts, B. and Vandyke, J., Sr.; "An Automated Vibration-Based Expert Diagnostic System"; Sound and Vibration; 27(9) (1993); pp. 14-20.

Worden, K.; "Damage Detection Using Multivariate Statistics, Part II: Kernel Density Estimation"; In Proc. Intl. Conf. On Noise and Vibration Engr. (ISMA-23); Leuven, Belguim (1998); 9 Pages.

Marron, J. S. and Ruppert, D.; "Transformations to Reduce Boundary Bias in Kernel Density Estimation"; J. Royal Statistical Society Ser. B; 56 (1994); pp. 653-671.

Park, B. U. and Turlach, B. A.; "Practical Performance of Several Data Driven Bandwidth Selectors"; Computational Statistics; 7 (1992); pp. 251-270.

Jones, M. C.; "Simple Boundary Correction for Kernel Density Estimation"; Statistics and Computing; 3 (1993); pp. 135-146.

Marcal, R. F. M., Negereiros, M., Susin, A. A. and Kovaleski, J. L.; "Detecting Faults in Rotating Machines"; IEEE Instrum. & Meas. Mag.; 3(4) (2000); pp. 24-26.

Forster, J. J.; "Estimating the Survival Distribution"; In Lecture Notes in Survival Analysis; School of Mathematics, University of Southampton, Highfield, UK; (2003); 27 Pages; http://www.maths.soton.ac.uk/staff/JJForster/Teaching/Math6021.

Caroni, C. and Prescott, P.; "Sequential Application of Wilk's Multivariate Outlier Test"; Appl. Statistics; 41; (1992); pp. 335-364.

Carey, V. J., Wagner, C. G., Walters, E. E. and Rosner, B. A.; "Resistant and Test-Based Outlier Rejection: Effects on Gaussian One-and Two-Sample Inference"; Technometrics; 39; (1997) pp. 320-330.

Berry, J. E., Proven Method for Specifying Both Spectral Alarm Bands as Well as Narrowband Alarm Envelopes Using Today's Condition Monitoring Software Systems:, Technical Associates of Charlotte, PC, Charlotte, NC, 4th edn. (2002), 59 Pages.

Duda, R. O., Hart, P.E. and Stork, D. G., Pattern Classification, "Nonparametric Techniques", John Wiley, NY, 2nd edn. (2001), Chapter 4, pp. 161-200.

Scott, D. W., "Multivariate Density Estimation: Theory, Visualization and Practice", John Wiley, NY (1992) Chapters 6 & 7.

Silverman, B.W., "Density Estimation for Statistics and Data Analysis", Chapman & Hall, London (1986), whole book.

Venables, W. N. and Ripley, B. D., Modern Applied Statistics with S. Springer, NY, 4th edn. (2002), Chapter 13.

Wand, M.P. and M. C. Jones, "Kernel Smoothing", Chapman & Hall/CRC, Boca Raton, FL (1995), Chapters 2, 3 and 4.

\* cited by examiner

| Kernel name | Definition | Plot |
|---|---|---|
| 1. Gaussian | $\kappa(u) = \frac{1}{\sqrt{2\pi}} e^{-u^2/2}$ |  |
| 2. Epanechnikov | $\kappa(u) = \frac{3}{4}(1 - u^2) 1_{\{|u|\leq 1\}}$ |  |
| 3. Biweight | $\kappa(u) = \frac{15}{16}(1 - u^2)^2 1_{\{|u|\leq 1\}}$ |  |
| 4. Triangle | $\kappa(u) = (1 - |u|) 1_{\{|u|\leq 1\}}$ |  |

Note: $1_{\{|u|\leq 1\}} \triangleq \begin{cases} 1 & \text{if } |u| \leq 1 \\ 0 & \text{otherwise} \end{cases}$

DETERMINING AMPLITUDE LIMITS FOR VIBRATION SPECTRA

BACKGROUND

The present invention relates generally to the field of detecting mechanical faults in HVAC equipment. More specifically, the present invention relates to a methodology for calculating vibration amplitude limits to detect mechanical faults in HVAC equipment such as chillers.

Timely detection, diagnosis and repair of mechanical problems in machinery such as heating, ventilating and air-conditioning (HVAC) systems is important for efficient operation. Chillers are important components of HVAC systems because they consume a large fraction of energy in a building and require a large capital investment. Severe mechanical faults in chillers typically results in expensive repairs and disruptions to the HVAC system during the repair period. Accordingly, chillers are generally monitored routinely to detect developing mechanical faults.

A common method for detecting and diagnosing mechanical faults is vibration analysis. By analyzing vibration data from different positions on a chiller, a vibration analyst can detect and diagnose mechanical faults in a machine. Vibration data is commonly available as a spectrum. The vibration analyst can determine a machine's condition by analyzing the vibration amplitude at different frequencies in the spectrum. A vibration analyst typically detects a mechanical fault that requires corrective action when the amplitudes in the vibration spectrum exceed "acceptable" limits. Under many current approaches, the acceptable limits are specified by rules-of-thumb or from a vibration analyst's experience. However, these approaches can be unreliable. For example, limits determined from an individual's experience can be incorrect or inconsistent. Similarly, limits specified by rules-of-thumb are typically generalized to apply to a large number of chillers and are therefore not likely relevant for some particular types of chillers.

Accordingly, there exists a need for a method of more accurately detecting mechanical faults without having to rely on an individual's knowledge of a system or general rule-of-thumb limits. In particular, it is desirable to be able to derive the limits from historical data using advanced statistical methods. By using statistics and historical data, the estimated limits may be based entirely on the vibration spectrum of each type of chiller. This approach easily allows updating of the amplitude limits when new vibration data from chillers is collected. In addition, because this approach uses statistical methods and not expert knowledge or "rules-of-thumb," it results in more consistent limits. Many vendors also use rudimentary statistics such as calculating the average and standard deviation of the data to estimate limits. Unfortunately, this approach can result in erroneous limits because vibration data usually don't follow a bell shaped (or Gaussian) probability distribution.

It would be advantageous to provide a method or the like of a type disclosed in the present application that provides any one or more of these or other advantageous features. The present invention further relates to various features and combinations of features shown and described in the disclosed embodiments. Other ways in which the objects and features of the disclosed embodiments are accomplished will be described in the following specification or will become apparent to those skilled in the art after they have read this specification. Such other ways are deemed to fall within the scope of the disclosed embodiments if they fall within the scope of the claims which follow.

SUMMARY

One embodiment of the present invention relates to a method for determining vibration amplitude limits to detect faults in mechanical equipment. The method comprises estimating a data probability distribution based on data for the mechanical equipment and utilizing the data probability distribution to calculate the vibration amplitude limits.

Another embodiment of the present invention relates to a method for detecting faults in a chiller based on vibration amplitude limits. The method comprises calculating vibration amplitude limits of the chiller using statistics and historical data for the chiller, estimating an at least two-dimensional density estimate, and weighting the historical data based on when the historical data was generated. The vibration amplitude limits are calculated as a function of frequency for an entire frequency spectrum.

Another embodiment of the present invention relates to a method for determining vibration amplitude limits of a mechanical device. The method comprises identifying a mechanical device and a frequency range for a spectrum to be analyzed, retrieving vibration spectra comprising individual spectrum for the mechanical device and the frequency range, calculating frequency for the individual spectrum, and identifying the individual spectrum with the smallest number of frequency lines. In addition, the method comprises calculating noise bandwidths and a largest noise bandwidth, removing outlier data, calculating conditional kernel density, and calculating vibration amplitude limits to detect faults in the mechanical device.

DETAILED DESCRIPTION

Figure 1:
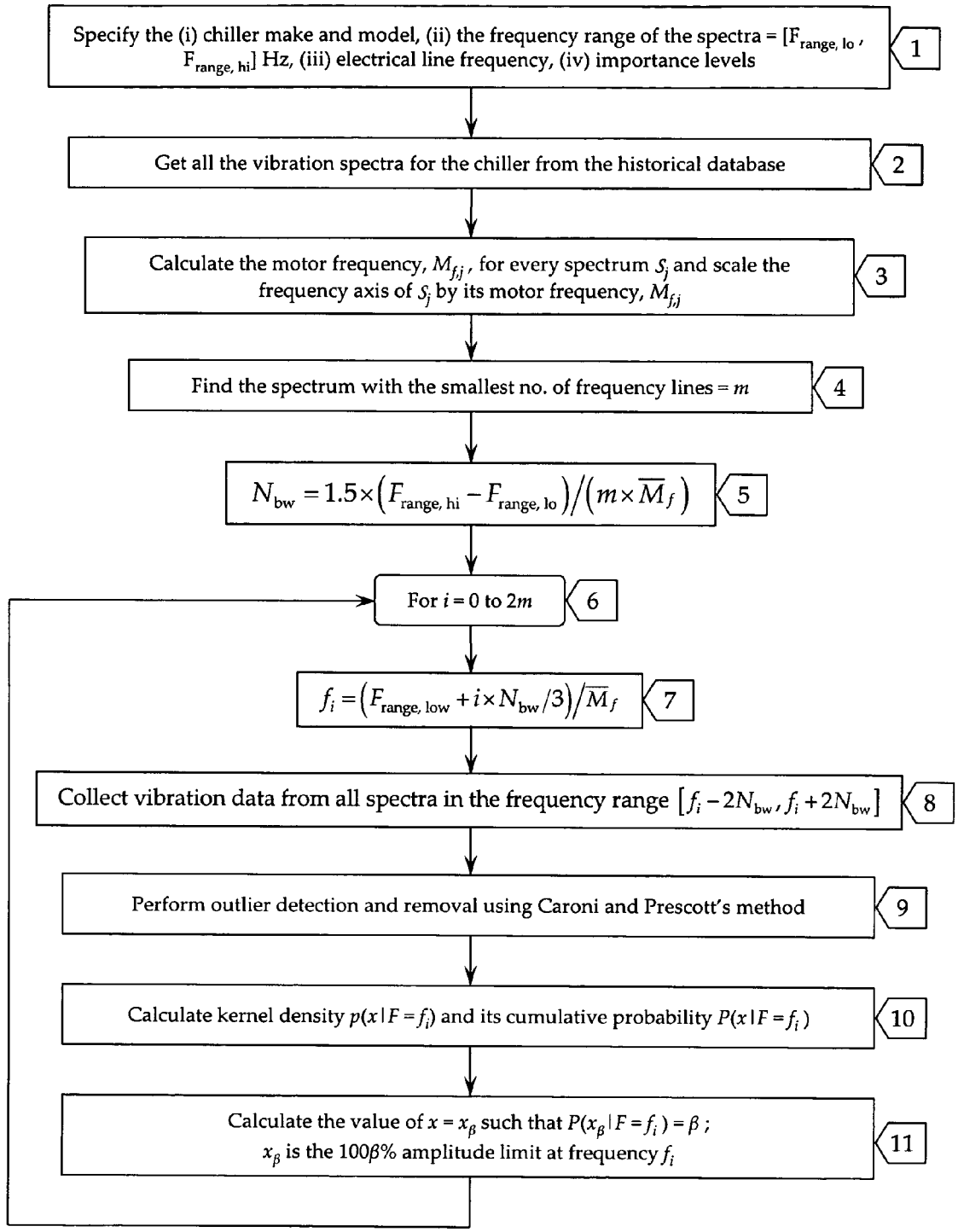
FIG. 1 is a block diagram illustrating a method of estimating vibration amplitude limits according to an exemplary embodiment.

Before explaining a number of exemplary embodiments of the invention in detail, it is to be understood that the invention is not limited to the details or methodology set forth in the following description or illustrated in the drawings. The invention is capable of other embodiments or being practiced or carried out in various ways. It is also to be understood that the phraseology and terminology employed herein is for the purpose of description and should not be regarded as limiting.

In general, the method described in this disclosure uses observed data to identify the probability distribution for the data and then uses the probability distribution to calculate limits for the data. For example, if a user finds that data follows a Gamma probability distribution, then the user can fit the data to a Gamma distribution, and then calculate the limits from the probability distribution. In many instances, vibration data do not follow a single type of distribution, and therefore there is a need to automatically generate the probability distribution from the data itself. A preferred embodiment of the invention calculates the probability distribution from the data using the kernel density estimation method, and then uses the estimated probability distribution to calculate the vibration limits.

An exemplary methodology for calculating vibration limits from historical data will now be discussed. This methodology is shown in FIG. 1. Step 1 requires user input while the rest of the steps are executed automatically.

At step 1, a vibration analyst specifies the chiller model for which the limits will be calculated as well as the frequency range of the spectrum. The frequency range of the spectrum is from $F_{range, low}$ to $F_{range, hi}$ Hz. The analyst also specifies the electrical line frequency (e.g., 60 Hz in North America, 50 Hz in Europe) and the importance levels for different frequencies. The importance levels for different frequencies is described in greater detail below.

At step 2, a historical database is queried to retrieve all spectra for the specified chiller make and model and the selected frequency range. The set "S" denotes the collection of n spectra retrieved from the historical data and the $j^{th}$ member of S is denoted as $S_j$. Each spectrum $S_j$ consists of frequency and amplitude data.

Figure 2:
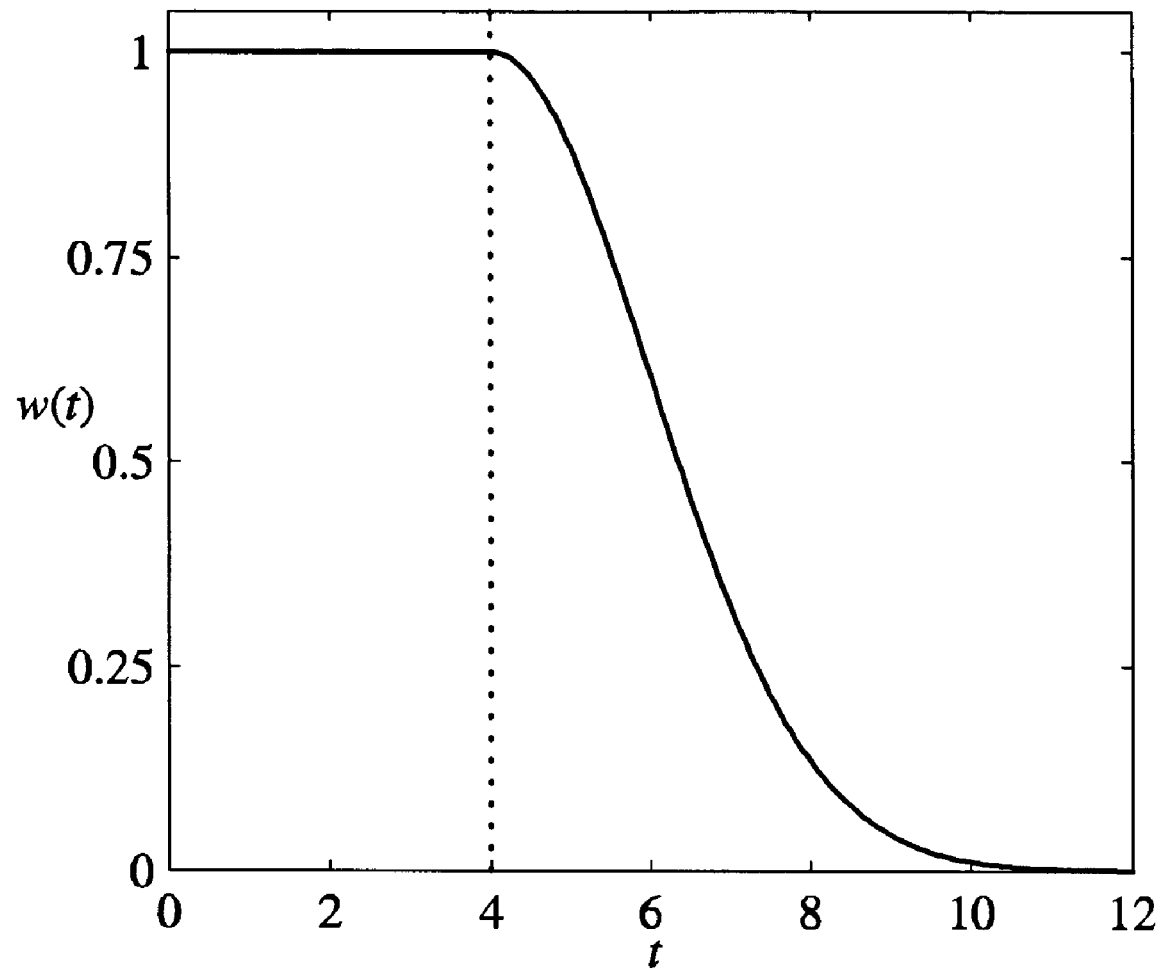
FIG. 2 is a diagram representing a function for removing old data from a dataset according to an exemplary embodiment.
Figure 3:
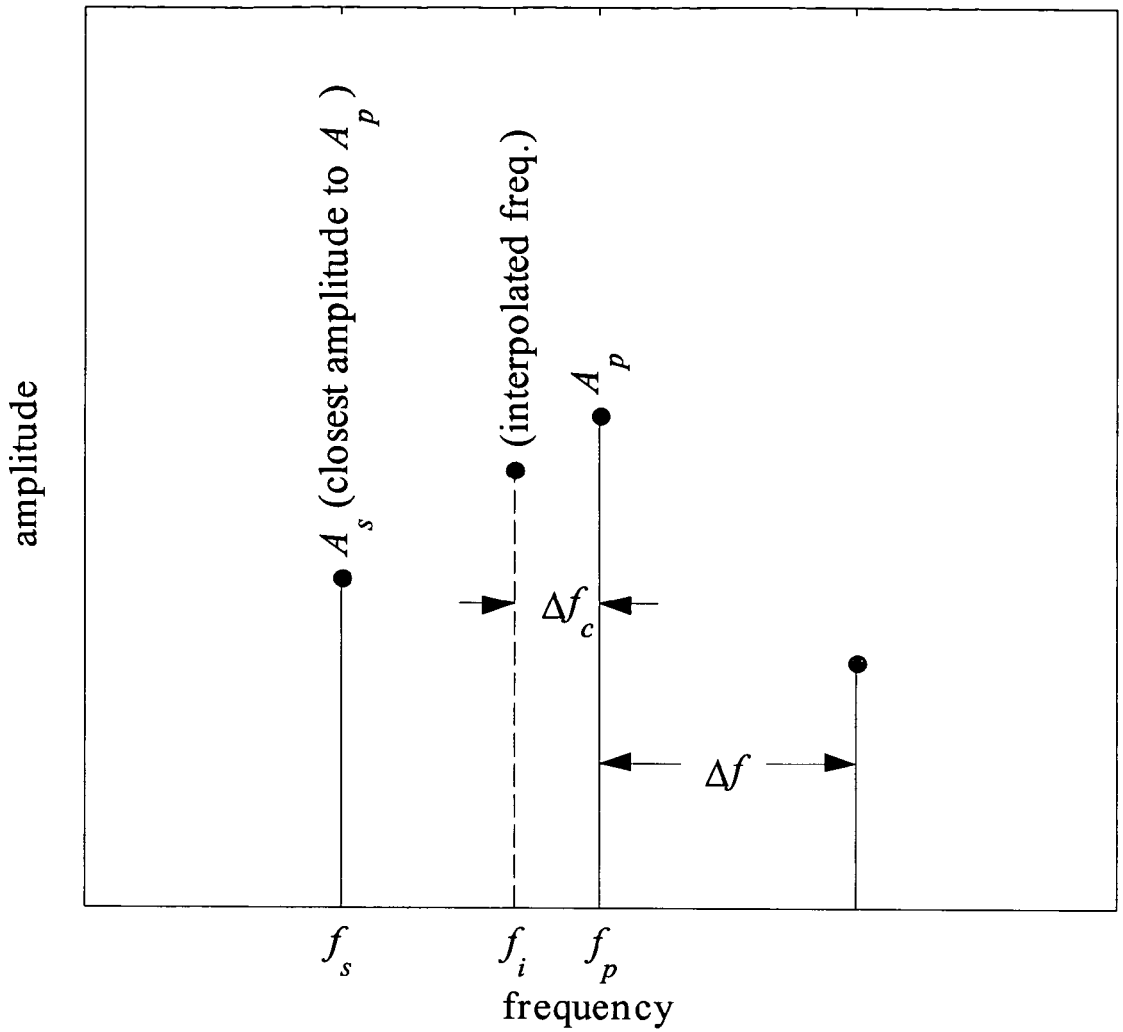
FIG. 3 is a diagram representing frequency interpolation according to an exemplary embodiment.

At step 3, a motor frequency $M_{f,j}$ (j=1, ..., n) is estimated for every spectrum $S_j$ and the frequency axis of $S_j$ is scaled by its motor frequency, $M_{f,j}$. Scaling the frequency axis by the motor frequency reduces the variation in the spectra due to differences in motor speeds. The motor frequency for every spectrum $S_j$ is calculated by first searching for the highest amplitude in the range 57–60 Hz (60 Hz is the electric line frequency in North America) and then using interpolation or another method to refine the frequency location of the peak. For example, an interpolation method may be used such as described by TECHNICAL ASSOCIATES, CONCENTRATED VIBRATION SIGNATURE ANALYSIS AND RELATED CONDITION MONITORING TECHNIQUES (2002). FIG. 2 illustrates this method. According to an exemplary embodiment illustrated in FIG. 3, while locating the motor frequency from the vibration spectrum, $f_p$ may be the frequency value of the highest peak in the range of 57–60 Hz. If $A_p$ is the amplitude at $f_p$, $f_s$ and $A_s$ are the frequency and amplitude of the line having an amplitude closest to $A_p$, and $\Delta f$ is the spacing between adjacent frequency lines, then the interpolated frequency $f_i$ may be calculated as:

$$\Delta f_c = \left( \frac{2A_s - A_p}{A_s + A_p} \right) \Delta f \quad (1)$$

$$f_i = \begin{cases} f_p + \Delta f_c & \text{if } f_s > f_p \\ f_p - \Delta f_c & \text{if } f_s < f_p \end{cases}$$

At step 4, the spectrum having the smallest number of frequency lines in S is found. If the number of frequency lines in spectrum $S_j$ is $m_j$, then $$m = \min_{1 \leq j \leq n} (m_j).$$

The value of m results in the calculation of the largest noise bandwidth $N_{bw}$ in S.

At step 5, the largest noise bandwidth $N_{bw}$ in S is calculated as:

$$N_{bw} = 1.5 \times \left[ \frac{F_{range,hi} - F_{range,lo}}{m \times \overline{M}_f} \right] \quad (2)$$

where $\overline{M}_f$ is the average value of the machine frequency for n spectra:

$$\overline{M}_f = \frac{1}{n} \sum_{j=1}^{n} M_{f,j} \quad (3)$$

According to an exemplary embodiment, the factor 1.5 is utilized assuming that a Hanning window was used for calculation of the spectrum from its time waveform.

At step 6, a loop begins for calculating the vibration amplitude limits at different frequencies. Although the limits can be calculated at any frequency, according to a preferred embodiment, the limits are calculated at frequencies spaced less than or equal to $N_{bw}/3$ to have a good resolution for the amplitude limit spectrum. Using results from step 4, there are 2 m+1 frequency values where the limits are calculated. Thus, step 6 implements a loop counter, i, from 0 to 2 m.

At step 7, a frequency value at which the amplitude limits will be estimated is calculated:

$$f_i = \frac{F_{range,lo} + i \times N_{bw}/3}{\overline{M}_f} \quad (4)$$

where $f_i$ is scaled by the average motor frequency.

At step 8, after the frequency value has been specified at step 7, vibration data are collected in the frequency range $f_i - 2N_{bw}$ to $f_i + 2N_{bw}$ from each spectrum $S_j$. In general, step 8 involves collecting vibration data in the range $f_i \pm (c \times N_{bw})$, where c is an integer $\geq 2$. The preferred value c=2 ensures that all data within the noise bandwidth is included in the density calculation and the computational load is at a minimum. A value of c<2 would result in elimination of data just outside the noise bandwidth. Recall that step 3 had scaled the frequency axis of each spectrum by its motor frequency. The data collected in step 8 has two dimensions: frequency and amplitude.

At step 9, outlier detection and removal for the two dimensional data collected from step 8 is implemented. Outlier removal is helpful to reduce the effect of unusual observations in limits calculation. Outliers are observations that appear to be inconsistent with the majority of data in a dataset. These observations are preferably removed from the data because they may corrupt the data analysis and can produce misleading results. For example, the average for the dataset, X={10, 9, 11, 8, 12, 50, 11, 30, 8}, is 16.6, even though the majority of the data are centered around 10. The observations 30 and 50 push the average to a higher value that suggests that most of the observations are centered around 16, which could be a misleading result. These observations also appear to be much larger than the majority of the data, and thus are called outliers. The average becomes 9.86 when these extreme observations are removed from the dataset, a result that is consistent with the majority of observations.

Many types of outlier detection procedures are known in the art. According to an exemplary embodiment, outlier removal using kernel density estimation may be utilized. According to a preferred embodiment, the sequential Wilk's multivariate outlier detection test may be utilized to determine outliers, as explained by C. CARONI AND P. PRESCOTT, *Sequential Application of Wilk's Multivariate Outlier Test*, APPL. STATISTICS 41, 355–64 (1992), hereinafter referred to as the "C and P method". The C and P method is well suited to the present embodiment because the data is two-dimensional (frequency and amplitude). The detailed procedure for detecting outliers using the C and P method will now be described.

Figure 4:
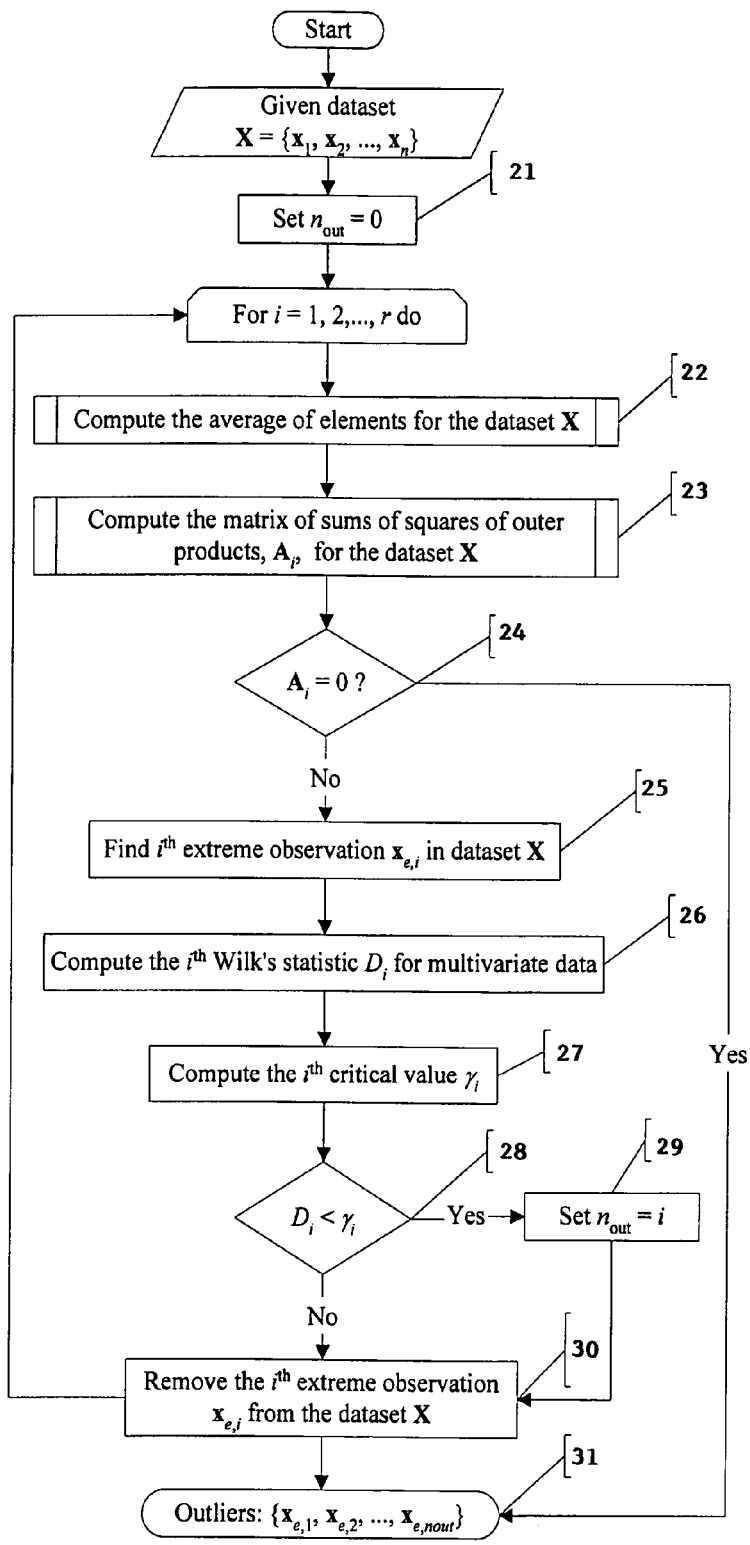
FIG. 4 is a block diagram illustrating a method of detecting outlier data from a dataset according to an exemplary embodiment.

The algorithm for detecting multivariate outliers in data is presented in FIG. 4. Given a dataset X={$x_1, x_2, \ldots, x_n$}, with n observations in d dimensions, and an estimate of the upper bound r for the number of outliers, the procedure presented in FIG. 4 identifies possible outliers in the dataset X. The descriptions of the steps of the procedure are presented below. At step 21, the number of outliers is initialized to zero by setting $n_{out}$=0. At step 22, the average $\bar{x}$ of the observations for dataset X is computed as:

$$\bar{x} = \frac{1}{n_i} \sum_{j=1}^{n_i} x_j, \qquad (5)$$

where $x_j$ is a member of the dataset X and n equals the number of observations in X.

At step 23, the matrix of sums of squares of outer products, $A_i$, for the dataset X is computed. The matrix sum of squares is determined as:

$$A_i = \sum_{j=1}^{n_i} (x_j - \bar{x})(x_j - \bar{x})^T \qquad (3)$$

At step 24, a test is performed to determine whether the matrix sum of squares is zero ($A_i$=0). If this matrix is zero, then all of the observations in dataset X have the same value and there are no outliers in the remaining observations in dataset X. To prevent division by the determinant of a zero matrix at step 25, the process moves to step 31 when the matrix sum of squares in step 24 equals zero. Otherwise, the process advances to step 25.

At step 25, the $i^{th}$ extreme observation $x_{e,i}$ in the dataset X is found. The most extreme observation $x_{e,i}$ can be identified where its removal results in the smallest value of $W_i=|A_i|/|A_{i-1}|$, where $A_{i-1}$ is the matrix obtained by removing the most extreme observation in the previous step. The notation |A| refers to the determinant of the matrix A.

At step 26, the $i^{th}$ extreme Wilk's statistic $D_i$ is computed. The Wilk's statistic is determined as:

$$D_i \triangleq \min\left(\frac{|A_i|}{|A_{i-1}|}\right) \qquad (7)$$

At step 27, the $i^{th}$ critical value i is computed. The C and P method utilizes the following relation for determining the critical value:

$$\gamma_i = \left[1 + \frac{d}{n-d-i} F_{d, n-d-i, (1-\alpha/(n-i+1))}\right]^{-1} \qquad (8)$$

where $F_{d, n-d-i, (1-\alpha/(n-i+1))}$ is the $100 \times (1-\alpha/(n-i+1))^{th}$ percentage point for the F distribution with d and (n–d–i) degrees of freedom, $\alpha$ is the probability of detecting outliers when there are no outliers, and d is the dimensionality of the data.

At step 28, a test is performed to determine if the $i^{th}$ critical value $D_i$ is less than the critical value $\gamma_i$ ($D_i < \gamma_i$), determined in step 27. At step 29, the number of outliers $n_{out}$ is set equal to i ($n_{out}$=i). At step 30, extreme observation $x_{e,i}$ is removed from the dataset X. After removing the extreme element $x_{e,i}$, the number of observations in the dataset X is n–i. If i equals r, then the process proceeds to step 31. Otherwise, i is incremented and the process returns to step 21. At step 31, the extreme observations that are outliers {$x_{e,1}, x_{e,2}, \ldots, x_{e,nout}$} are identified. The first $n_{out}$ extremes identified at step 25 are considered outliers. However, not all the extreme values determined at step 25 are outliers.

The C and P method is designed for Gaussian data. However, vibration data does not always follow a Gaussian distribution. Despite this limitation, the C and P method may still be used to process the vibration data because the approach enables the detection of observations that have very high amplitudes compared to a majority of the data.

The maximum number of expected outliers in the data, r, is another parameter of the C and P method. A large value for r means that more data points are expected to be outliers, which results in a large computational effort. According to an exemplary embodiment, r may be set to be the largest integer less than 0.2×n, where n is the number of spectra in the set S to reduce the computational load.

Figure 5:
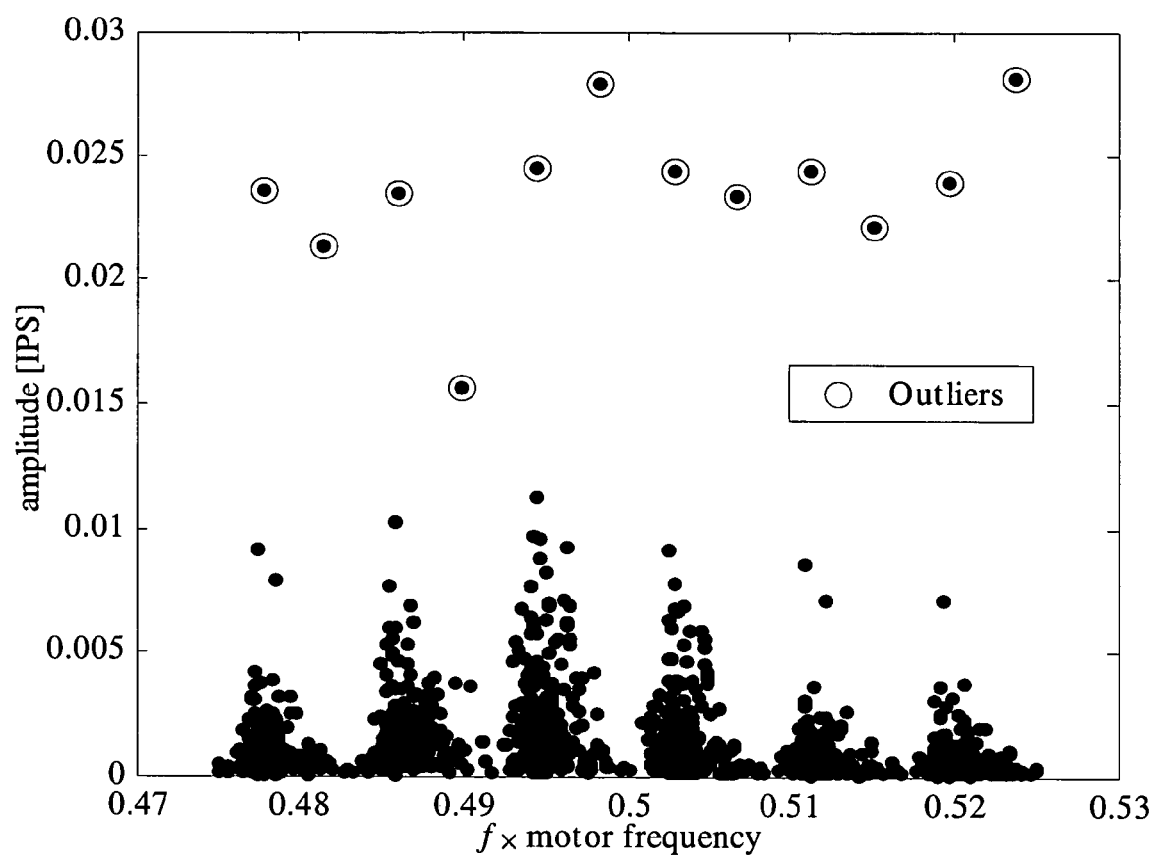
FIG. 5 is a diagram representing the application of multivariate outlier removal from vibration data according to an exemplary embodiment.

The vibration database contains data from acceptable as well as faulty machines. Outlier removal is performed to remove the unusual values that are a result of severe faults and/or measurement errors. After outlier removal, the database may still contain data from machines that have large vibration levels, but these data should be included for calculation of amplitude limits in order to observe the full range and distribution of vibration amplitudes. The application of the C and P method is presented in FIG. 5 for sample data from a chiller at f=0.5.

Referring back to FIG. 1, at step 10, the conditional kernel density $p(x|F=f_i)$ is calculated, where x is the amplitude and F represents the frequency axis. An exemplary procedure for calculating $p(x|F=f_i)$ from the two dimensional data is discussed below. At step 10, the cumulative probability function, $P(x|F=f_i)$, is also calculated by numerically integrating the density $p(x|F=f_i)$ from zero to x:

$$P(x|F=f_i) = \int_0^x p(z|F=f_i)dz.$$

The amplitude axis is divided into a fine grid of 1000 points and $P(x|F=f_i)$ is calculated numerically at each of these grid points. This procedure makes calculating the inverse of $P(x|F=f_i)$ at step 11 relatively easy.

At step 11, the value $x_\beta$ is calculated such that $P(x|F=f_i)=\beta$, where $\beta$ is a specified probability cutoff. Thus, $x_\beta$ is the $100\times\beta$ % confidence limit for the vibration amplitude. Typical values for $\beta$ are 0.95, 0.99, etc. An exemplary methodology for choosing the value for $\beta$ is discussed below. The value of $x_\beta$ can be calculated by a look-up table of $P(x|F=f_i)$ and x grid values from step 10. After the completion of step 11, the process returns back to the beginning of the "For" loop at step 6 and the amplitude limits for a new frequency value are calculated. A spectral amplitude limit envelope is obtained at the termination of the "For" loop. The vibration analyst can compare the spectrum for a new machine with the calculated limit envelope to determine if any amplitude in the new spectrum violates the limits. If any of the amplitudes violate the limits, then a machine fault is present. In addition, the frequency location of a limit violation provides the vibration analyst with clues about the possible cause of the fault.

The kernel density estimation method briefly discussed at step 10 above will now be described in greater detail. The kernel density method is described in detail by M. P. WAND AND M. C. JONES, KERNEL SMOOTHING (1995). The kernel density estimation method is also known as the Parzen windows method for density estimation. It attempts to estimate an unknown probability density for a given dataset X. The probability density estimate at a point x for a one-dimensional dataset with n data points is given by:

$$p(x) = \frac{1}{nh}\sum_{j=1}^n \kappa\left(\frac{x-x_j}{h}\right) \quad (9)$$

where, $x_j$ is the $j^{th}$ observation of the dataset X, h is called the bandwidth that characterizes the spread of the kernel, and $\kappa(\bullet)$ is a kernel density function that is symmetric and satisfies the condition:

$$\int_{-\infty}^{\infty} \kappa(u)du = 1 \quad (10)$$

Figure 6:
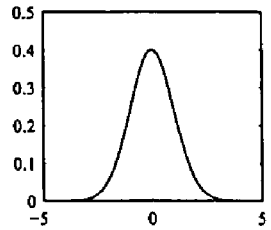
FIG. 6 is a diagram illustrating a variety of kernel functions according to an exemplary embodiment.
Figure 6:
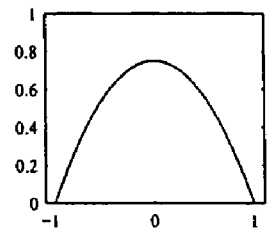
Figure 6:
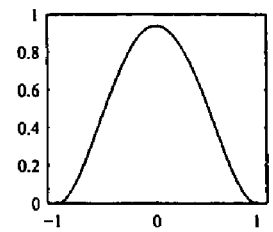
Figure 6:
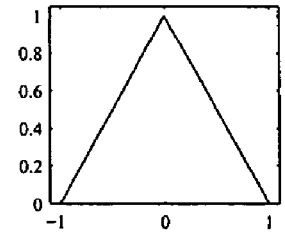

Some common univariate kernel density functions, $\kappa(\bullet)$, are listed in FIG. 6. The notation $1_{\{|u|\leq 1\}}$ means:

$$1_{\{|u|\leq 1\}} \triangleq \begin{cases} 1 & \text{if } |u| \leq 1 \\ 0 & \text{otherwise} \end{cases} \quad (11)$$

To calculate the kernel density for two-dimensional vibration data (e.g., frequency and amplitude directions), an expression should be utilized for the kernel density estimation in two or more dimensions. In general, Equation (9) is extended to d dimensions by replacing the univariate kernel $\kappa(u)$ by a d-dimensional kernel K (u), and the bandwidth h by a bandwidth matrix H. Then, the d-dimensional kernel density estimate is written as:

$$p(x) = \frac{1}{n}\sum_{j=1}^n |H|^{-1/2} K(H^{-1/2}(x-x_j)) \quad (12)$$

where $|\bullet|$ denotes the matrix determinant. There are two known ways of constructing the multivariate density in Equation (12) from univariate kernel functions. One option is to use a spherically symmetric multivariate kernel $K^S(u)=c_{\kappa,d}\kappa((u^tu)^{1/2})$, where $c_{\kappa,d}$ is a constant dependent on the univariate kernel $\kappa(\bullet)$, and the dimensionality. A second option is to use a multivariate product kernel $$K^P(u) = \prod_{i=1}^d \kappa(u_i).$$

Although $K^S(\bullet)$ and $K^P(\bullet)$ are usually different, the difference between the kernel densities estimated using $K^S(\bullet)$ and $K^P(\bullet)$ is typically very small. The product kernel $K^P(\bullet)$ is easier to implement in software, particularly when boundary correction (described below) is not required in all dimensions. Thus, the product form of the multivariate kernel is used to calculate the density according to a preferred embodiment.

For the two-dimensional vibration data, F and x denote the frequency and the amplitude dimensions, respectively. Then, the expression for the kernel density using the product kernel in these two dimensions is written as:

$$p(x,F) = \frac{1}{n}\sum_{j=1}^n \frac{1}{h_f h_x}\kappa\left(\frac{F-f_j}{h_f}\right)\kappa\left(\frac{x-x_j}{h_x}\right) \quad (13)$$

In Equation (13), $h_f$ and $h_x$ are bandwidths of the frequency and amplitude kernels, and $f_j$ and $x_j$ are the frequency and amplitude values of the $j^{th}$ observation in the dataset, respectively.

To calculate the vibration amplitude limits at a given frequency value F=f, the conditional probability density $p(x|F=f_i)$ is first calculated from the joint probability density $p(x, F)$. Conditional density is then used to calculate the limits. The conditional probability density of the vibration amplitude (x) for a given frequency value (F=f) is calculated as:

$$p(x \mid F = f) \triangleq \frac{p(x, F = f)}{\int_{x=0}^{\infty} p(x, F = f) dx} \quad (14)$$

The kernel density estimation method has two important design parameters including the choice of the kernel function and its bandwidth. First, although the choice of the kernel function is not particularly important based on the efficiencies of different kernel functions, the choice is useful from a computational perspective for large data sets. For example, a Gaussian kernel requires a much larger computational effort than the Epanechnikov kernel. Also, a Gaussian boundary kernel requires the numerical calculation of integrals while the expression for the Epanechnikov boundary kernel is obtained analytically.

The Epanechnikov kernel has the lowest asymptotic mean integrated squared error (AMISE) in estimating the kernel density as well as a low computational cost. Thus, the Epanechnikov kernel is the preferred kernel for estimating the probability density.

The second useful parameter is the kernel bandwidth. The kernel bandwidth calculation methods can be divided into two broad categories: (i) first generation rules-of-thumb, and (ii) second generation methods that produce bandwidths close to the optimal value.

A rule of thumb (ROT) using the sample variance and the inter-quartile-range (IQR) may be used to estimate the bandwidth of the kernels. According to an exemplary embodiment, a robust estimate of the kernel width, h, is, $$h = 0.9 \times \lambda \times n^{-1/5} \quad (15)$$

where, $$\lambda = \min\left(\sigma, \frac{IQR}{1.349}\right) \quad (16)$$

The quantity $\sigma$ is the sample standard deviation. The inter-quartile-range (IQR) is computed as the difference between the 75th percentile (Q3) and the 25th percentile (Q1) of the data. Thus, IQR=Q3−Q1. The quantity represents the width estimate based on the inter-quartile range and the factor 1.349 is the inter-quartile-range for a Gaussian distribution with zero mean and unit standard deviation. This expression is valid for univariate data.

Second generation methods are designed to produce bandwidths that are close to the optimum but require a larger computational effort. According to an exemplary embodiment, the Sheather-Jones bandwidth selection method may be used to calculate the kernel bandwidth. This method calculates the bandwidth by using a series of "direct-plug-in" equations and is described by S. J. SHEATHER AND M. C. JONES, *A Reliable Data-Based Bandwidth Selection Method for Kernel Density Estimation*, J. ROYAL STATISTICAL SOC. SER. B, v. 53, 683–90 (1991).

The Sheather-Jones direct-plug-in (SJ-dpi) method calculates the kernel bandwidth by using fourth and higher order derivatives of the kernel function and requires them to be non-zero and finite. Because the third and higher-order derivatives of the Epanechnikov kernel function presented in this disclosure are zero, the SJ-dpi method cannot be used directly to calculate the bandwidth for the Epanechnikov kernel. To solve this problem, an exemplary method uses a result called the theory of equivalent kernels, which is described by D. W. SCOTT, MULTIVARIATE DENSITY ESTIMATION: THEORY, VISUALIZATION AND PRACTICE (1992). By using this theory, the bandwidth calculated using one kernel function can easily be transformed to another kernel function. For example, if the bandwidth is calculated assuming a Gaussian kernel, then the equivalent bandwidth for the Epanechnikov kernel is:

$$h_{Epanech} = 2.214 \times h_{Gaussian} \quad (17)$$

Because the Gaussian kernel function has infinite number of non-zero and finite derivatives, the method calculates the bandwidth using the Gaussian kernel and then transforms it for the Epanechnikov kernel using Equation (17). The bandwidths $h_1$ and $h_2$ of two kernels $\kappa_1$ and $\kappa_2$ are related as:

$$\frac{h_1}{h_2} = \left[\frac{R(\kappa_1)/\mu_2^2(\kappa_1)}{R(\kappa_2)/\mu_2^2(\kappa_2)}\right]^{1/5} \quad (18)$$

where $\mu_2(\kappa)$ is the second order moment and $R(\kappa)$ is the roughness of the kernel $\kappa$.

The Sheather-Jones direct-plug-in method assuming a Gaussian kernel is described as follows. First, calculate the estimate of scale ($\lambda$) for the data. It is preferred to use the smaller of the sample standard deviation ($\sigma$) and the normalized interquartile range (IQR) as a scale estimate:

$$\lambda = \min\left(\sigma, \frac{IQR}{1.349}\right) \quad (19)$$

Second, calculate the normal-scale approximation, $$\hat{\psi}_8^{NS} = \frac{105}{32\sqrt{\pi}\lambda^9} \quad (20)$$

where n is the sample size. Third, calculate the first approximation of the bandwidth:

$$g_1 = \frac{-2\kappa^{(6)}(0)}{\mu_2(\kappa)\hat{\psi}_8^{NS} n} = \left[\frac{30}{\sqrt{2\pi}\,\hat{\psi}_8^{NS} n}\right]^{1/9} \quad (21)$$

where $\kappa^{(6)}(0)$ is the sixth derivative of the kernel function $\kappa$ evaluated at zero, and $\mu_2(\kappa)$ is the second-order moment for the kernel $\kappa$. Here $\kappa$=Gaussian kernel is assumed. Fourth, calculate the second approximation of the bandwidth using the fourth derivative of the kernel and the kernel estimator $\hat{\psi}_6(g_1)$:

$$g_2 = \frac{-2\kappa^{(4)}(0)}{\mu_2(\kappa)\hat{\psi}_6(g_1)n} = \left[\frac{-6n}{2s_1 - 15n}\right]^{1/7} g_1 \quad (22)$$

where:

$$s_1 = \left[\sum_{i=1}^{n-1}\sum_{j=i+1}^{n} e^{-t_{i,j}/2}[([t_{i,j} - 15]t_{i,j} + 45)t_{i,j} - 15]\right], \text{ and} \quad (23)$$

$$t_{i,j} = \left(\frac{x_i - x_j}{g_1}\right)^2 \quad (24)$$

Finally, calculate the bandwidth using the kernel roughness function R(κ) and the kernel estimator $\hat{\psi}_4(g_2)$:

$$h = \frac{R(\kappa)}{\mu_2(\kappa)^2 \hat{\psi}_4(g_2) n} = \left[\frac{n}{\sqrt{2}\,(2s_2 + 3n)}\right]^{1/5} g_2 \quad (25)$$

where:

$$s_2 = \left[\sum_{i=1}^{n-1} \sum_{j=i+1}^{n} e^{-t'_{i,j}/2}([t'_{i,j} - 6]t'_{i,j} + 3)\right], \text{ and} \quad (26)$$

$$t'_{i,j} = \left(\frac{x_i - x_j}{g_2}\right)^2 \quad (27)$$

Figure 7:
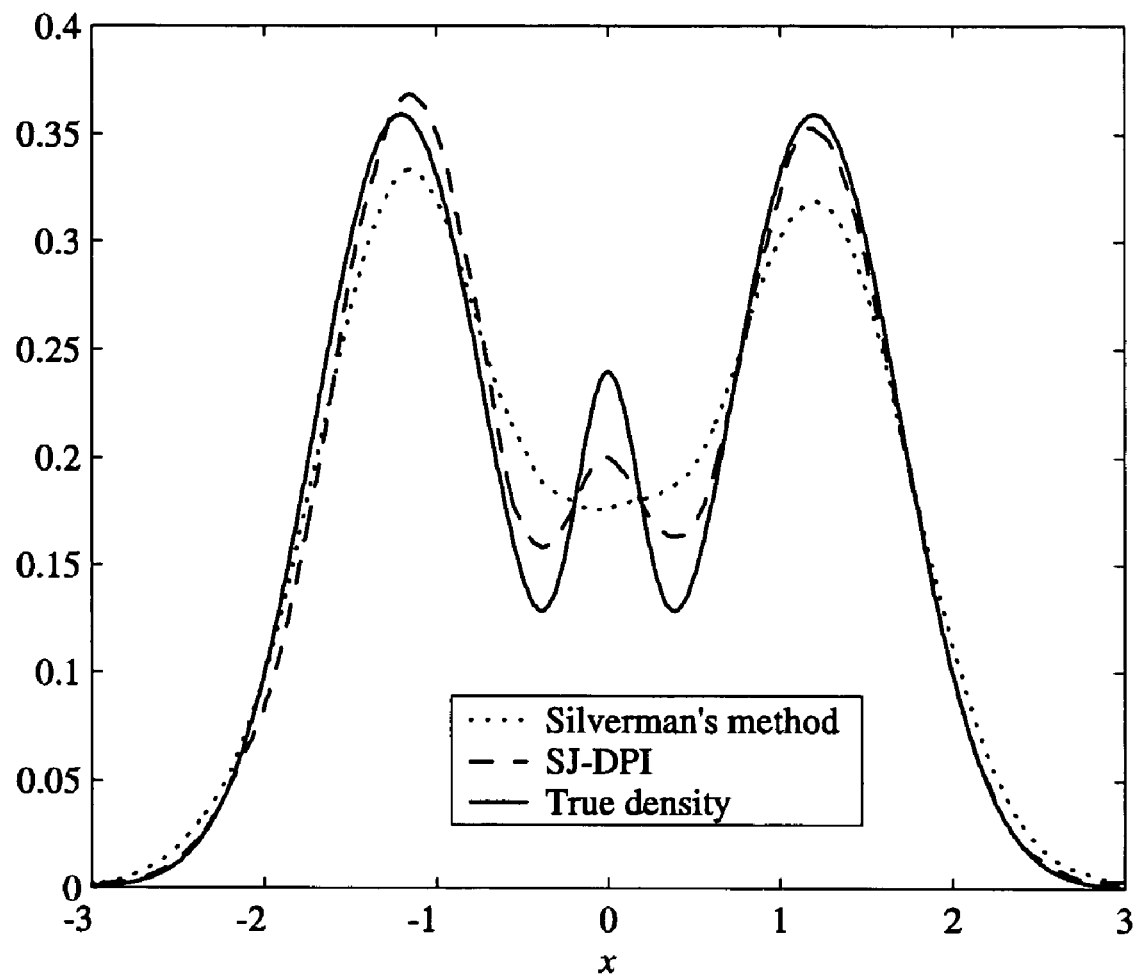
FIG. 7 is a diagram comparing kernel density estimates obtained using different bandwidth selection methods according to an exemplary embodiment.

A comparison of the kernel density estimates using the first generation method and Sheather-Jones direct-plug-in bandwidths is presented in FIG. 7 for a multi-modal density $$p(x) = \frac{9}{20} N\!\left(-\frac{6}{5}, \left(\frac{1}{2}\right)^2\right) + \frac{9}{20} N\!\left(\frac{6}{5}, \left(\frac{1}{2}\right)^2\right) + \frac{1}{10} N\!\left(0, \left(\frac{1}{5}\right)^2\right).$$

The kernel density estimate using the first generation bandwidth method completely misses the middle peak at x=0, while the density estimate using the SJ-dpi bandwidth is able to reveal the tri-modal structure of the data. Thus, FIG. 7 shows the improvement of the SJ-dpi method over the first generation bandwidth calculation method.

The difference between the actual density and the calculated kernel density is called the bias of the kernel density. Kernel density estimates can have large bias near boundaries when the data have lower or upper bounds. For the present embodiment on chiller vibration data, the vibration amplitudes are always positive, that is, the data have a lower boundary at zero. To correct the error in estimating density near the lower boundary (near zero), a different set of kernels may be used near the boundary. For kernels with a [−1, 1] support, such as the Epanechnikov kernel, boundary kernels may be calculated as:

$$\kappa^L(u, a) = \left[\frac{v_2(a) - v_1(a)u}{v_0(a)v_2(a) - v_1^2(a)}\right]\kappa(u) 1_{\{-1 < u < a\}} \quad (28)$$

where $\kappa^L(\bullet)$ is the boundary kernel, $\kappa(\bullet)$ is a kernel function defined in Table 1 with a [−1, 1] support, u=(x−$x_i$)/h and a=x/h. The coefficients $v_l(a)$(l=0, 1, 2) are defined as:

$$v_l(a) = \int_{-1}^{a} u^l \kappa(u)\,du \quad (29)$$

For the Epanechnikov kernel, the coefficients $v_l(a)$ are:

$$v_0(a) = \frac{1}{4}(-a^3 + 3a + 2) \quad (30)$$

$$v_1(a) = \frac{3}{16}(-a^4 + 2a^2 - 1)$$

$$v_2(a) = \frac{1}{20}(-3a^5 + 5a^3 + 2)$$

Figure 8:
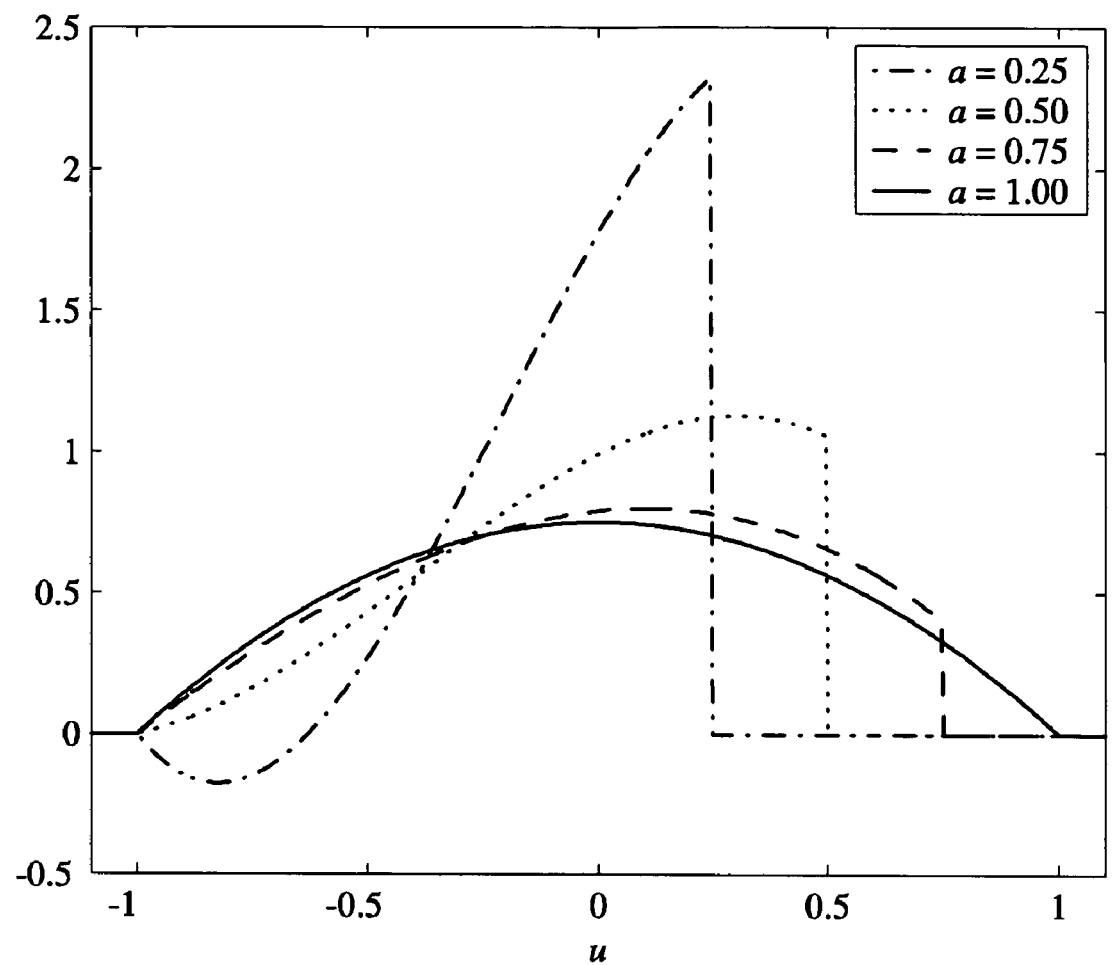
FIG. 8 is a diagram illustrating Epanechnikov boundary kernels for different values according to an exemplary embodiment.

The boundary kernels are used in Equation (13) when a<1 and the standard kernel is used for a≧1. The Epanechnikov boundary kernels for different values of the parameter a=x/h are presented in FIG. 8.

Because the boundary kernels have negative values, the density estimate using these kernels can also be negative. Thus, in order to obtain a positive density estimate, the negative density may be truncated to zero and then the density estimate may be re-scaled as:

$$p(x) \leftarrow \frac{p(x)}{\int_0^\infty p(x)\,dx} \quad (31)$$

such that p(x) now satisfies p(x)≧0 and $$\int_0^\infty p(x)\,dx = 1.$$

In addition to boundary kernels, two other methods for reducing boundary bias may be utilized such as data reflection and data transformation. The data reflection method makes the density estimate "consistent" but still produces estimates with a large boundary bias. Thus, boundary kernels are needed to reduce the bias at the boundary to the same level as that in the interior. The data transformation method is more complicated and computationally intensive than the boundary kernels approach. Thus, the boundary kernels is a preferred method to reduce the boundary bias in kernel density estimation.

Figure 9:
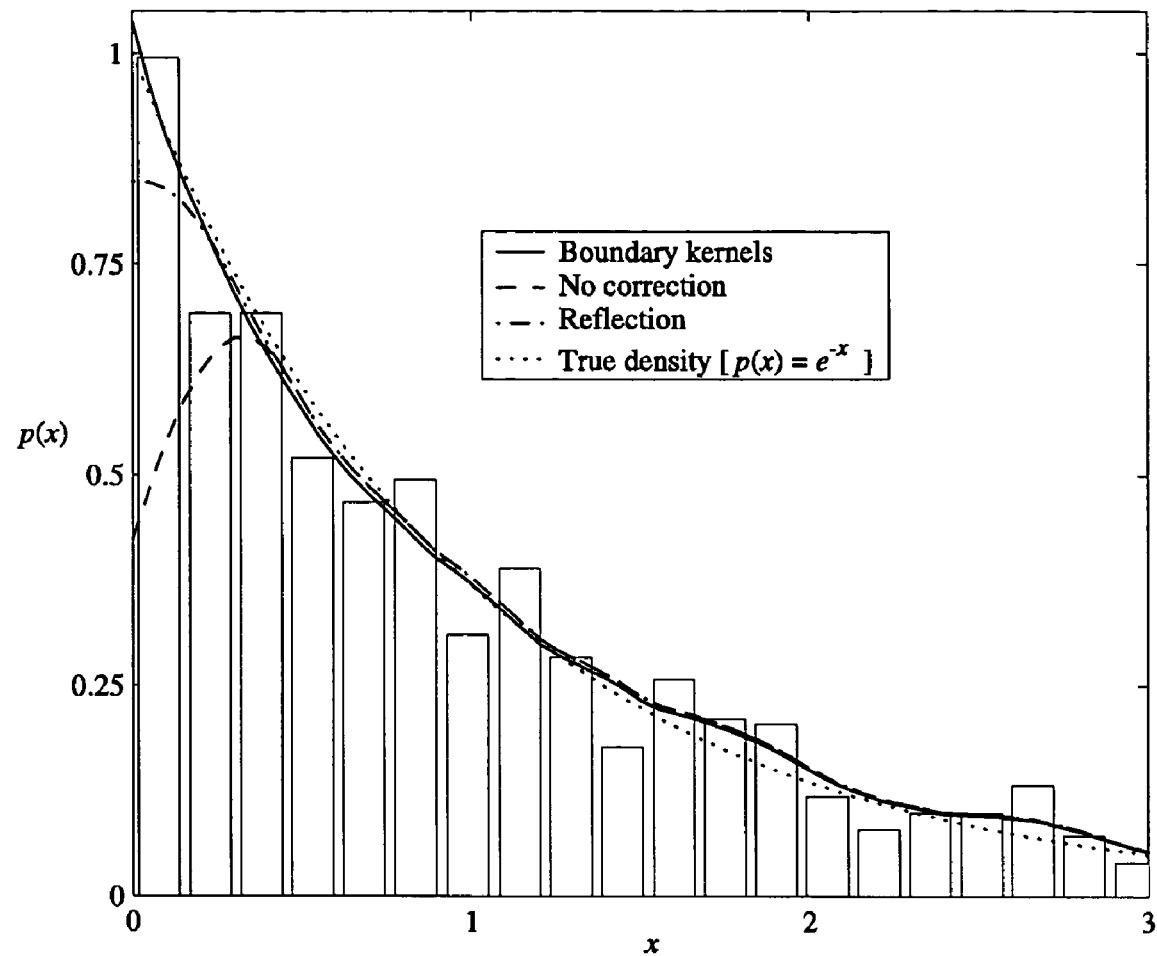
FIG. 9 is a diagram illustrating the effect of boundary bias on kernel density estimation according to an exemplary embodiment.

A simple example illustrating the effect of boundary bias on kernel density estimation is presented in FIG. 9 for the exponential density p(x)=$e^{-x}$. The exponential density has a lower boundary at x=0 so that:

$$p(x) = \begin{cases} e^{-x} & \text{if } x \geq 0 \\ 0 & \text{if } x < 0. \end{cases} \quad (32)$$

In this example, one thousand observations were sampled from the exponential distribution and the data were used to estimate the kernel density. FIG. 9 shows that with no boundary bias correction, the kernel density estimate near the boundary is very different from the true density. The estimate is better with the reflection method, while the boundary kernels approach produces very accurate results.

Once the conditional probability density for the amplitude is known, it is used to calculate limits as follows. The limits for the vibration amplitudes may be estimated by first numerically integrating the estimated conditional density p(x|F=f) in Equation (14) using Simpson's rule to obtain the cumulative conditional density function P(x|F=f). A cutoff value, β, is also specified for the cumulative probability function. Then, the amplitude limit $x_\beta$ is estimated by calculating the inverse of the cumulative probability density function P(x|F=f) at a probability value of β:

$$P(x|F=f) = \beta \quad (26)$$

Typically, a vibration analyst sets three levels of amplitude limits that are referred to as the "alert," "alarm" and "danger" limits. Common values for the probability cutoffs for these limits are β=0.95, 0.99 and 0.995 respectively.

TABLE 1

Probability cutoff limits for different importance levels.

| Importance Level | β Alert | Alarm | Danger |
|---|---|---|---|
| 1 (low) | 0.9995 | 0.9999 | 0.99995 |
| 2 | 0.999 | 0.9995 | 0.9999 |
| 3 | 0.995 | 0.999 | 0.9995 |
| 4 | 0.99 | 0.995 | 0.999 |
| 5 (high) | 0.95 | 0.99 | 0.995 |

There are special frequencies in the vibration spectrum that are called "diagnostic frequencies" because they correspond to the characteristic frequencies of different machine components. Vibration analysts commonly analyze vibrations near these frequencies to detect mechanical faults. Some examples of diagnostic frequencies for chillers are motor, compressor, gear-mesh and blade-pass frequencies.

In the exemplary methodology, a vibration analyst can specify importance levels for different frequencies in the vibration spectrum. For example, for a Chiller A, the motor frequencies are assigned high importance while the blade-pass frequencies and other parts of the spectrum have relatively lower importance levels. The probability cutoffs are determined from the importance level of a frequency.

A five level importance scheme may be used where each importance level corresponds to a different value for the probability cutoff for each of the alert, alarm and danger limits. According to an exemplary embodiment, an importance level of "one" means low importance, while a value of "five" means high importance. The probability cutoff values for the five importance levels are presented in Table 1. Typically, the diagnostic frequencies of a machine (e.g., motor, blade-pass, gear-mesh frequencies, etc.) have high importance levels, while other parts of the spectrum have lower importance. Hence, the default importance level for the entire spectrum except the diagnostic frequencies is set to "one" (low importance).

Low importance levels typically have high probability cutoff values. These high probability cutoffs result in higher amplitude limits for frequencies that are not very important. Higher amplitude limits for less important frequencies will result in a lower number of false alarms. Thus, an importance level scheme such as described herein allows the vibration analyst to focus on the important frequencies while retaining the ability to detect faults when unusually high amplitudes are observed at less important frequencies.

Examination of the foregoing importance level scheme reveals that the probability cutoff limits have a sharp discontinuity at the diagnostic frequencies. For example, the importance level changes from "one" to "five" at the motor frequencies and results in an abrupt change in the probability cutoff values. This abrupt change in the probability cutoffs may result in a sharp discontinuity for the amplitude limit envelope at the diagnostic frequencies. To have a continuous transition between the cutoff limits, a weighting scheme is used to smooth the probability cutoff values near the diagnostic frequencies:

$$\beta_f = \beta_{def} + (\beta_{diag} - \beta_{def}) \times \exp\left[-\frac{1}{2}\left(\frac{f - f_{diag}}{4N_{bw}}\right)^2\right] \quad (34)$$

Figure 10:
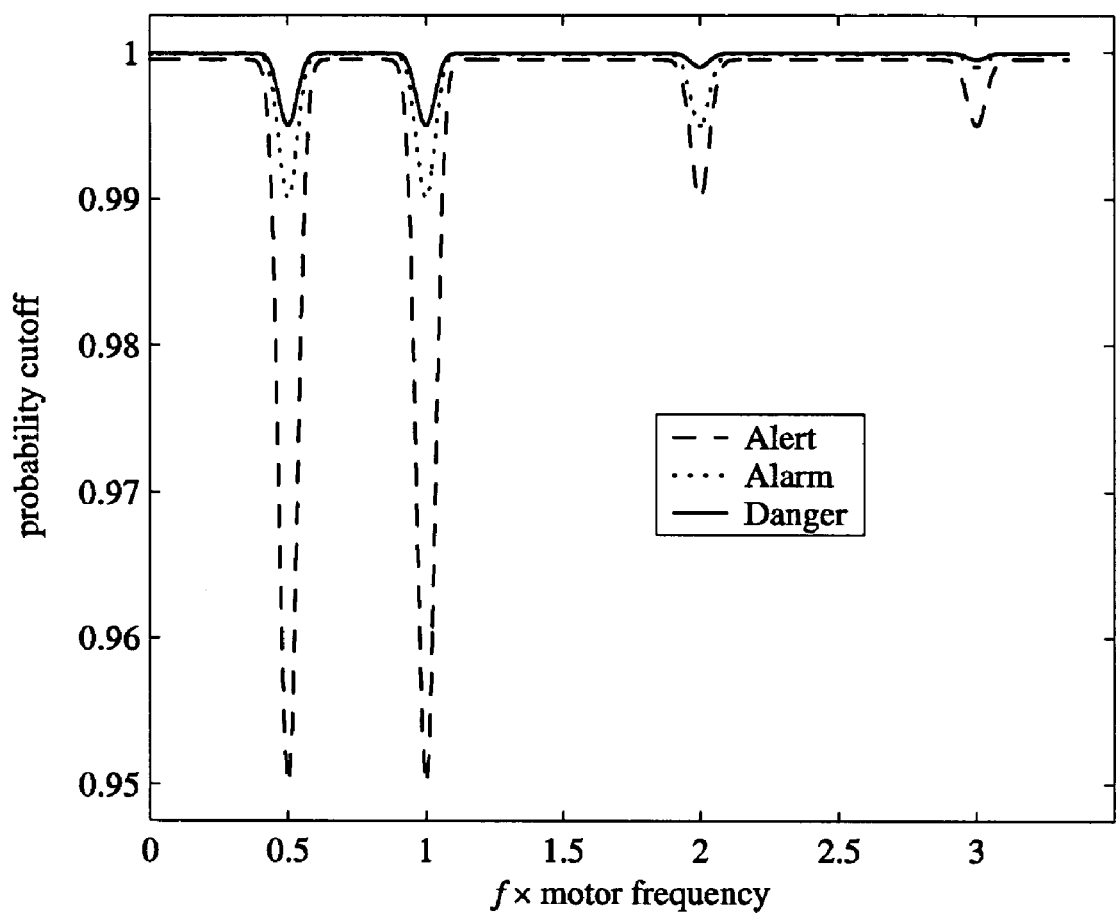
FIG. 10 is a diagram illustrating the effect of weighting on the alert, alarm, and danger confidence levels with diagnostic frequencies for a chiller according to an exemplary embodiment.

In Equation (34), $\beta_f$ is the probability cutoff value for frequency F=f, $\beta_{def}$ is the default probability cutoff corresponding to the lowest importance level, and $\beta_{diag}$ is the probability cutoff limit for the closest diagnostic frequency $f_{diag}$. If the frequency f is between two diagnostic frequencies that are closer than $12 \times N_{bw}$ from each other, then linear interpolation may be used to determine the probability cutoff value between the two diagnostic frequencies, otherwise Equation (34) is used. This situation occurs while calculating the probability cutoff values between 2×motor and electrical frequencies. FIG. 10 shows the probability cutoff levels for the 0–200 Hz spectrum with diagnostic frequencies of half, one, two and three times the motor frequency. The importance levels for these diagnostic frequencies are "five," "ive," "four" and "three" respectively.

According to an exemplary embodiment, vibration spectra for two chillers (Chiller A and B) were obtained and outlier removal and density estimation were performed for every frequency line using methods such as described above. In addition, the limits were calculated for every frequency line.

Figure 11:
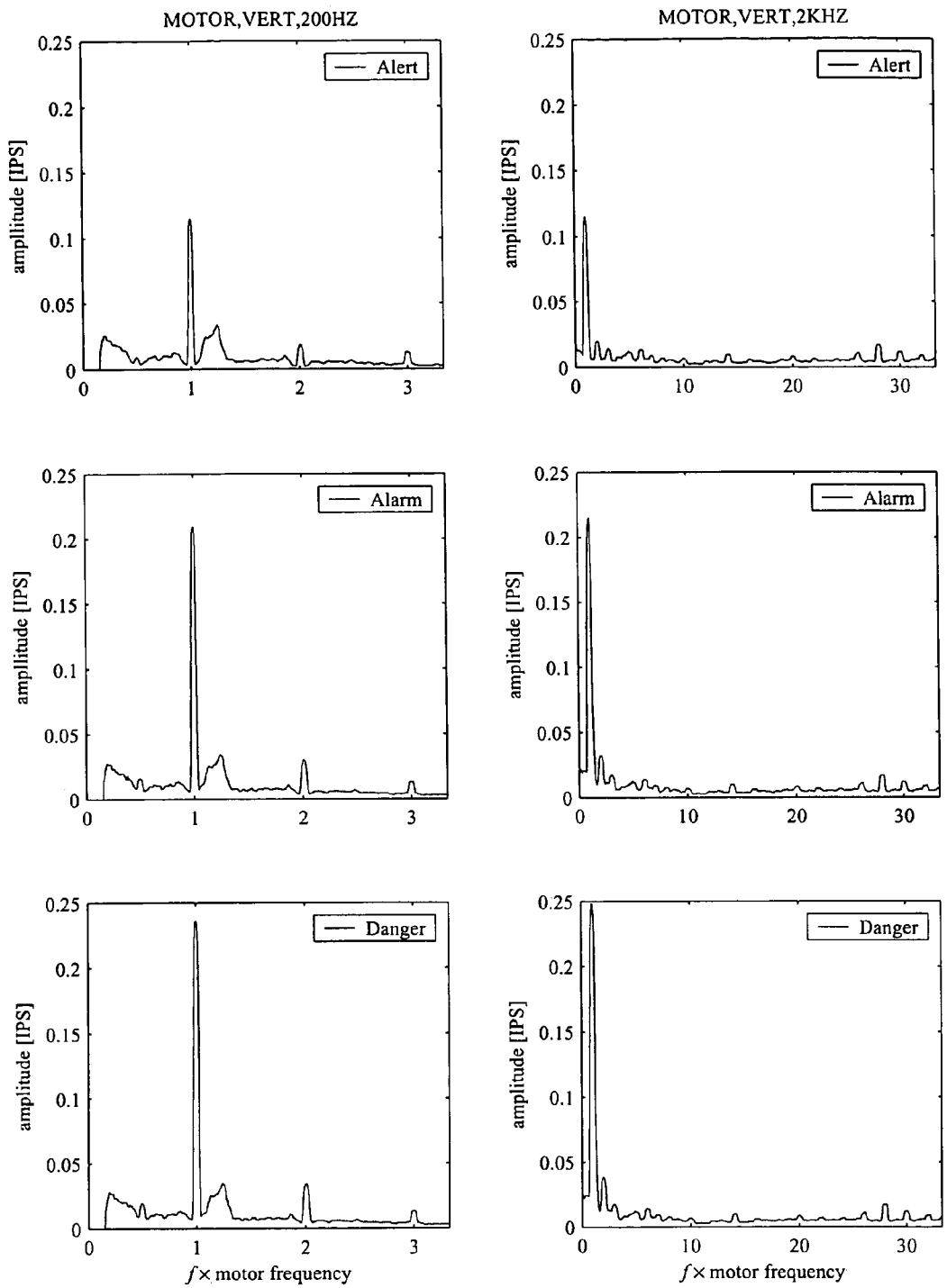
FIG. 11 is a diagram illustrating amplitude limit envelopes for the motor-vertical position of a chiller according to an exemplary embodiment.
Figure 12:
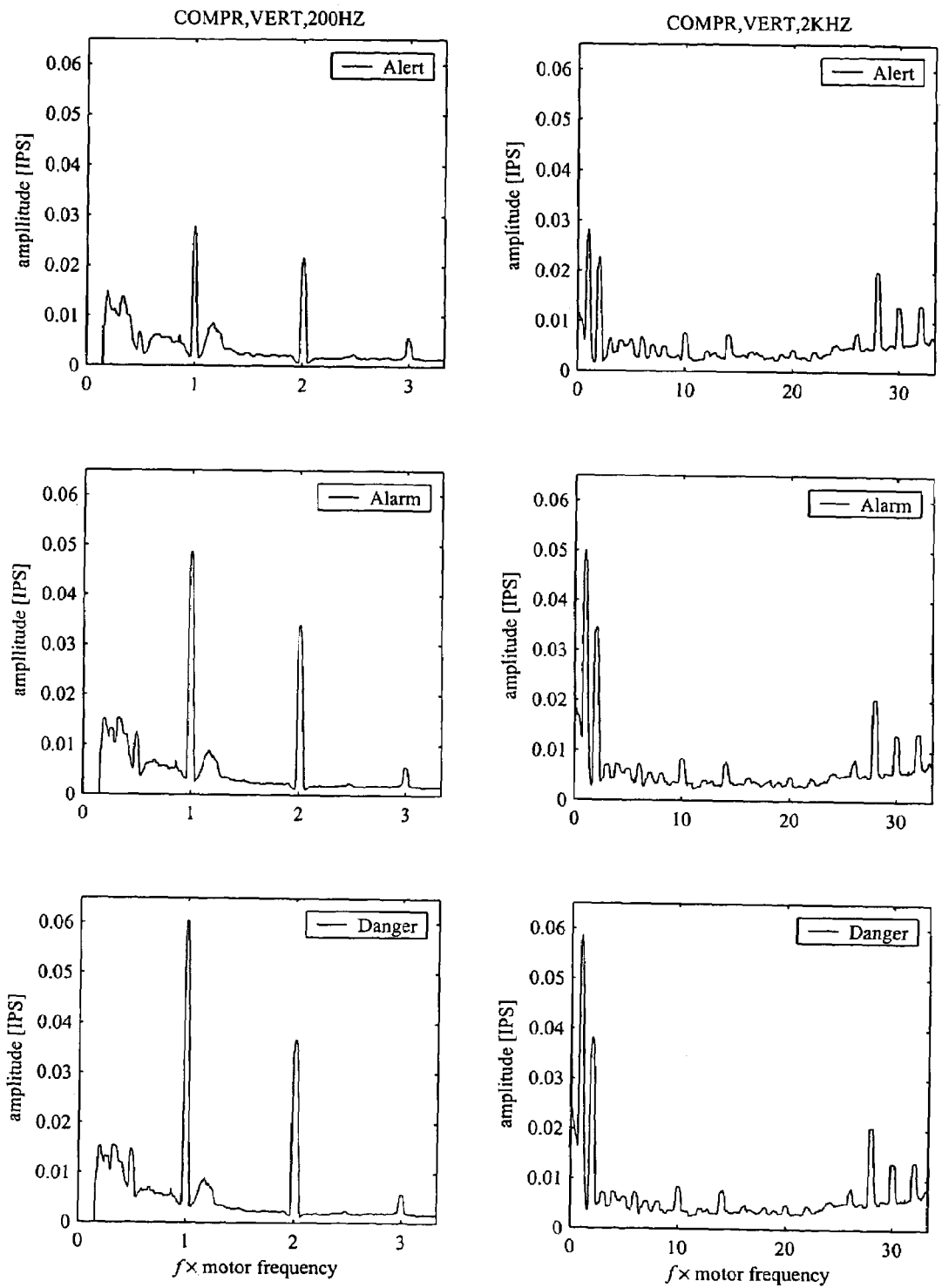
FIG. 12 is a diagram illustrating amplitude limit envelopes for the compressor-vertical position of a chiller according to an exemplary embodiment.

The results for the motor and compressor vertical positions for Chiller A are presented in FIGS. 11 and 12 respectively. These figures show that although it is useful to detect problems at the diagnostic frequencies of motor harmonics, sub-harmonics and blade-pass frequencies, other frequency ranges play a role. For example, a high amplitude of vibration in frequency band 1–1.5×motor frequency may signal a bearing fault that will be missed if only the diagnostic frequencies were analyzed. The exemplary approach allows the vibration analyst to quickly compare the entire spectrum with the limit envelopes to detect problems in any part of the spectrum.

It is important to note that the above-described preferred embodiments are illustrative only. Although the invention has been described in conjunction with specific embodiments thereof, those skilled in the art will appreciate that numerous modifications are possible without materially departing from the novel teachings and advantages of the subject matter described herein. Accordingly, these and all other such modifications are intended to be included within the scope of the present invention as defined in the appended claims. The order or sequence of any process or method steps may be varied or re-sequenced according to alternative embodiments. In the claims, any means-plus-function clause is intended to cover the structures described herein as performing the recited function and not only structural equivalents but also equivalent structures. Other substitutions, modifications, changes and omissions may be made in the design, operating conditions and arrangements of the preferred and other exemplary embodiments without departing from the spirit of the present invention.

What is claimed is:

1. A method for detecting faults in a chiller based on vibration amplitude limits, comprising:
    calculating vibration amplitude limits of the chiller using statistics and historical data for the chiller;
    estimating an at least two-dimensional density estimate; and
    weighting the historical data based on when the historical data was generated;
    wherein the vibration amplitude limits are calculated as a function of frequency for an entire frequency spectrum.

2. The method of claim 1 further comprising removing outlier data.

3. The method of claim 2 wherein the at least two-dimensional density estimate utilizes frequency and amplitude directions of the frequency spectrum.

4. The method of claim 3 wherein the at least two-dimensional density estimate is a d-dimensional kernel density estimate.

5. The method of claim 4 wherein the d-dimensional kernel density estimate for point x of a dataset with n data points is given by:

$$p(x) = \frac{1}{n}\sum_{j=1}^{n}|H|^{-1/2}K(H^{-1/2}(x-x_j))$$

where, $x_j$ is the $j^{th}$ observation of the dataset, K (u) is a d-dimensional kernel, H is a bandwidth matrix, and |•| denotes a matrix determinant.

6. The method of claim 4 further including obtaining vibration spectra comprising individual spectrum for the chiller from a database.

7. The method of claim 6 further comprising calculating a frequency for the individual spectrum and identifying an individual spectrum having the smallest number of frequency lines.

8. The method of claim 7 further comprising calculating noise bandwidths and a largest noise bandwidth.

9. The method of claim 8 further comprising collecting vibration data from all spectra in a given frequency range.

10. The method of claim 1 further comprising calculating a conditional kernel density.

11. The method of claim 10 wherein calculating the conditional kernel density comprises estimating an unknown probability density for a given dataset.

12. A method for determining vibration amplitude limits of a mechanical device comprising:
    identifying a mechanical device and a frequency range for a spectrum to be analyzed;
    retrieving vibration spectra comprising individual spectrum for the mechanical device and the frequency range;
    calculating frequency for the individual spectrum;
    identifying the individual spectrum with a smallest number of frequency lines;
    calculating noise bandwidths and a largest noise bandwidth;
    removing outlier data;
    calculating conditional kernel density; and
    calculating vibration amplitude limits to detect faults in the mechanical device.

13. The method of claim 12 wherein the mechanical device comprises a chiller for an HVAC system.

14. The method of claim 12 wherein the vibration spectra for the mechanical device and the frequency range is obtained from a database.

15. The method of claim 14 wherein calculating conditional kernel density comprises estimating an unknown probability density for a given dataset.

16. The method of claim 15 wherein the probability density estimate at a point x for a one-dimensional dataset with n data points is given by:

$$p(x) = \frac{1}{nh}\sum_{j=1}^{n}\kappa\left(\frac{x-x_j}{h}\right)$$

where, $x_j$ is the $j^{th}$ observation of the dataset, h is a bandwidth that characterizes a spread of the kernel, and $\kappa(\bullet)$ is a kernel density function that is symmetric and satisfies the condition:

$$\int_{-\infty}^{\infty}\kappa(u)du = 1.$$

17. The method of claim 15 wherein the kernel density estimate is at least a two-dimensional kernel density estimate utilizing frequency and amplitude directions of the frequency spectrum.

18. The method of claim 17 wherein a d-dimensional kernel density estimate is given by:

$$p(x) = \frac{1}{n}\sum_{j=1}^{n}|H|^{-1/2}K(H^{-1/2}(x-x_j))$$

where K (u) is a d-dimensional kernel, H is a bandwidth matrix, and |•| denotes a matrix determinant.

19. A method for determining vibration amplitude limits to detect faults in mechanical equipment, comprising:
    estimating a data probability distribution based on data for the mechanical equipment;
    utilizing the data probability distribution to calculate the vibration amplitude limits, such that the data probability distribution is calculated using statistics and historical data of the mechanical equipment including using a kernel density method, wherein the kernel density method comprises calculating conditional kernel density including estimating an unknown probability density for a given dataset, the probability density estimate at a point x for a one-dimensional dataset with n data points being given by:

$$p(x) = \frac{1}{nh}\sum_{j=1}^{n}\kappa\left(\frac{x-x_j}{h}\right)$$

where, $x_j$ is the $j^{th}$ observation of dataset X, h is a bandwidth that characterizes a spread of the kernel, and $\kappa(\bullet)$ is a kernel density function that is symmetric and satisfies the condition:

$$\int_{-\infty}^{\infty}\kappa(u)du = 1;$$

removing outlier data; and calculating the vibration amplitude limits as a function of frequency for a substantial portion of the frequency spectrum.

20. The method of claim 19 wherein the kernel density estimate is a two-dimensional kernel density estimate utilizing frequency and amplitude directions of the frequency spectrum.

21. The method of claim 20 wherein a d-dimensional kernel density estimate is generally written as:

$$p(x) = \frac{1}{n}\sum_{j=1}^{n} |H|^{-1/2} K(H^{-1/2}(x - x_j))$$

where K (u) is a d-dimensional kernel, H is a bandwidth matrix, and |•| denotes a matrix determinant.

* * * * *